United States Patent [19]

Frank et al.

[11] Patent Number: 5,382,732
[45] Date of Patent: Jan. 17, 1995

[54] 2,5-BIS(1,1-DIALKOXY-2-PROPYL)-2,5-DIHYDROFURANS, THE PREPARATION THEREOF AND THE USE THEREOF FOR THE PREPARATION OF CAROTENOIDS

[75] Inventors: Juergen Frank, Limburgerhof; Udo Rheude, Heidelberg; Bernhard Schulz, Schwetzingen; Joachim Paust, Neuhofen; Eckhard Hickmann, Dannstadt-Schauernheim, all of Germany

[73] Assignee: BASF Aktiengesellschaft, Ludwigshafen, Germany

[21] Appl. No.: 67,618

[22] Filed: May 27, 1993

Related U.S. Application Data

[62] Division of Ser. No. 866,590, Apr. 10, 1992, Pat. No. 5,300,658.

Foreign Application Priority Data

Apr. 15, 1991 [DE] Germany .................. 4112272

[51] Int. Cl.[6] .............................. C07C 403/06
[52] U.S. Cl. .................................. 585/351
[58] Field of Search .............. 585/351; 568/483, 475, 568/476; 205/254; 549/502

[56] References Cited

U.S. PATENT DOCUMENTS

| | | | |
|---|---|---|---|
| 2,750,418 | 6/1956 | Clauson-Kaas | 568/483 |
| 3,634,518 | 1/1972 | Buddrus | 585/351 |
| 4,105,855 | 8/1978 | Schulz et al. | 585/351 |
| 4,916,250 | 4/1990 | Babler | 585/351 |
| 5,110,423 | 5/1992 | Little et al. | 205/254 |

Primary Examiner—Asok Pal
Assistant Examiner—P. Achutamurthy
Attorney, Agent, or Firm—Keil & Weinkauf

[57] ABSTRACT

A process of preparing symmetric $C_{40}$-carotenoids by reacting a $C_{15}$-triphenylphosphonium salt of the formula

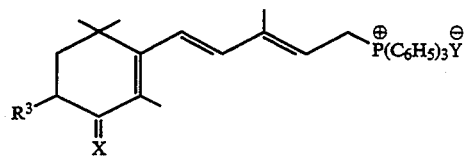

and a 2,5-bis(1,1-dialkoxy-2-propyl)-2,5-dihydrofuran to form a reaction product containing a diacetyl and a triphenylphosphonium salt, adding a strong base to the reaction product to convert the triphenylphosphonium salt to a carbenium ion, hydrolyzing the diacetyl to a dialdehyde, subjecting the dialdehyde and the carbenium ion to a Wittig reaction to prepare a Wittig reaction product, and converting the Wittig reaction product to the $C_{40}$-carotenoid by acid treatment.

1 Claim, No Drawings

2,5-BIS(1,1-DIALKOXY-2-PROPYL)-2,5-DIHYDROFURANS, THE PREPARATION THEREOF AND THE USE THEREOF FOR THE PREPARATION OF CAROTENOIDS

This is a division of application Ser. No. 07/866,590, filed Apr. 10, 1992 now U.S. Pat. No. 5,30,658.

BACKGROUND OF THE INVENTION

1. Field of the Invention

The present invention relates to 2,5-bis(1,1-dialkoxy-2-propyl)-2,5-dihydrofurans of the formula I

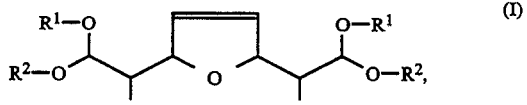

where $R^1$ and $R^2$ can be identical or different and are alkyl of 1 to 4, preferably 1 or 2, carbons, to a simple process for the preparation thereof and to the use thereof for the preparation of 2,7-dimethyl-2,4,6-octatrienedial and of symmetric carotenoids.

2. Description of the Related Art

An advantageous process for the preparation of symmetric carotenoids which are in demand, such as the $C_{40}$-carotenoids of the formula IV β-carotene, canthaxanthin and astaxanthin, is based on linkage at both ends of 2,7-dimethyl-2,4,6-octatrienedial to the appropriate $C_{15}$-triphenylphosphonium salts of the formula V in a Wittig reaction (cf. DE 28 01 908).

The $C_{10}$-dialdehyde 2,7-dimethyl-2,4,6-octatrienedial required for this purpose is prepared in the prior art from methylglyoxal dimethyl acetal and 1,4-bis(dimethylphosphono)-2-butene by a Wittig-Horner reaction and acetal hydrolysis ( cf., for example, Angew, Chem, 89 (1977) 437-443).

The processes for preparing the precursors methylglyoxal acetal and 1,4-bis(dimethylphosphono )-2-butene require elaborate safety techniques and thus make the $C_{10}$-dialdehyde a costly component in the synthesis.

Thus, methylglyoxal acetal is obtained from acetone in two stages in which first the acetone is nitrosated with methyl nitrite and then the oxime is reacted with methanol to give the required product, 1,4-Bis(dimethylphosphono )-2-butene is obtained from 2-butene-1,4-diol via 1,4-dibromo-2-butene, which is very objectionable from the health point of view, and reaction thereof with trimethyl phosphite. The byproduct is bromomethane which is likewise a health hazard.

Furthermore, it has been disclosed in CH 321 106 that the $C_{10}$-dialdehyde can also be prepared by reactions between fumaraldehyde acetals or malealdehyde acetals and alkyl propenyl ethers. The intermediate $C_{10}$-diether acetals are hydrolyzed in acid medium to the $C_{10}$-dialdehyde which can be isolated as crystals.

The disadvantage of this process is that the fumaraldehyde and malealdehyde are prepared from acetylenic precursors by partial hydrogenation. The person skilled in the art is aware that such partial hydrogenations are difficult to carry out and occur with sufficient selectivity only when exactly defined reaction conditions are strictly observed.

It is furthermore evident from CH 321 106 that the $C_{10}$-diether acetals are sensitive to heat, cannot be purified and therefore are preferably processed undistilled to the $C_{10}$-dialdehyde.

Besides the economic disadvantage of its high price, the $C_{10}$-dialdehyde has the physical disadvantage of a great tendency to crystallize, which does facilitate its isolation but subsequently interferes with its reaction with other components. Therefore large amounts of solvent and large apparatus are needed when it is used in carotenoid syntheses.

SUMMARY OF THE INVENTION

It is an object of the present invention to find a more advantageous way of preparing the $C_{10}$-dialdehyde or a $C_{10}$-dialdehyde equivalent and thus of preparing symmetric carotenoids which overcomes the prior art disadvantages.

DESCRIPTION OF THE PREFERRED EMBODIMENTS

We have found that this object is achieved by preparing the 2,5-bis(1,1-dialkoxy-2-propyl)-2,5-dihydrofurans of the formula I, according to the invention, which can be prepared advantageously and converted straightforwardly into the $C_{10}$-dialdehyde or into symmetric carotenoids, which allows the problems previously associated with the isolation and use of the $C_{10}$-dialdehyde to be solved in a surprisingly simple way.

The present invention therefore relates not only to the 2,5-dihydrofurans of the formula I but also to a process for preparing them, which comprises reacting a 2,5-dialkoxy-2,5-dihydrofuran of the formula II

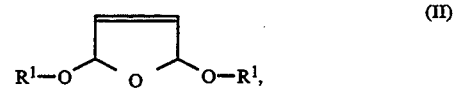

where $R^1$ is alkyl of 1 to 4 carbons, preferably methyl or ethyl, in the presence of an acid catalyst and in the presence or absence of a solvent, at from $-78°$ C. to the boiling point of the reaction mixture, with an alkyl propenyl ether of the formula III

where $R^2$ is alkyl of 1 to 4 carbons, preferably methyl or ethyl.

The 2,5-dialkoxy-2,5-dihydrofurans of the formula II required as starting materials are intermediates in the preparation of the biocide succinaldehyde and thus are available industrially on a large scale. They are obtained, for example, by electrochemical oxidation of furan in alkanols.

Suitable acid catalysts for the process according to the invention are protic acids or Lewis acids. The presence of Lewis acids is particularly advantageous.

Particularly suitable protic acids are halogen-, phosphorus- or sulfur-containing acids. Examples which may be mentioned are HCl, HBr, $HClO_4$, $H_3PO_4$, $H_2SO_4$, $CH_3SO_3H$ or p-toluenesulfonic acid.

The term Lewis acid means according to the invention a halide of an element of group IIA, IIIA or IVA or IIB, IVB or VIII of the periodic table. Examples are $MgCl_2$, $MgBr_2$, $BF_3$, $AlCl_3$, $SnCl_4$, $ZnCl_2$, $ZnBr_2$, $TiCl_4$, $FeCl_3$, $CoCl_2$ and $CoBr_2$. However, it is also possible to catalyze the reaction by combining two substances which do not on their own have catalytic activity. Systems of this type have recently been disclosed in the literature (Chem. Lett. (1989) 1277–1280).

The reaction can be carried out either in the presence or in the absence of a solvent, advantageously in the presence of a solvent. Suitable solvents are substances which dissolve both the catalyst and the reaction components and which are stable under the reaction conditions. Preferably used are esters of a $C_1$–$C_4$-carboxylic acid with a $C_1$–$C_4$-alkanol, especially ethyl acetate. However, $C_3$–$C_6$-ethers such as diethyl ether, 1,2-dimethoxyethane, 1,2-diethoxyethane or cyclic ethers such as tetrahydrofuran or 1,4-dioxane, and $C_2$–$C_7$-nitriles such as acetonitrile, propionitrile or benzonitrile, and $C_3$–$C_8$-ketones such as acetone, methyl ethyl ketone, diethyl ketone, methyl isobutyl ketone, cyclohexanone or acetophenone can also be used very satisfactorily as solvent. A carboxylic ester such as ethyl acetate is advantageously used as solvent.

The choice of the solvent is based on considerations of expediency and has no influence in principle on the success of the reaction.

The reaction is generally carried out at from $-78°$ C. to the boiling point of the solvent used, preferably at from $-30°$ to $+30°$ C., in particular at from $-15°$ to $+15°$ C.

In the choice of the dialkoxydihydrofuran and of the alkyl propenyl ether it is possible to employ any desired components, there being no need to use particular derivatives. $R^1$ and $R^2$ in the formula I can be identical or different depending on whether the alkoxy in the dihydrofuran is identical to or different from that in the propenyl ether. If starting materials with different alkoxy groups are reacted, e.g. 2,5-dimethoxydihydrofuran and ethyl propenyl ether, the reaction product is a random mixture of the acetals of the formula I with methoxy and ethoxy groups.

The process according to the invention is expediently carried out by introducing the catalyst into the solvent and adding the components of the formula II and III at the most suitable temperature for the reaction.

The compounds of the formula I, according to the invention, are liquids which can be distilled without decomposition.

The $C_{10}$-dialdehyde 2,7-dimethyl-2,4,6-octatrienedial can be prepared by treating the mixture of isomers obtained according to the invention with acid in the presence of water. The $C_{10}$-dialdehyde can then be either isolated or, preferably, treated directly, without isolation, with the required triphenylphosphonium salt and thus subjected to a Wittig reaction to give a symmetric carotenoid. It is very particularly advantageous in this connection that, in many cases, the acidic action of the aqueous solution of an alkyl- or alkenyltriphenylphosphonium bisulfate is sufficient for the hydrolysis of the bisacetals of the formula I and for the cleavage of the dihydrofuran ring of the compounds of the formula I. After the cleavage of the acetal, the Wittig reaction is carried out by adding a suitable base. Thus, beta-carotene, which is in demand, is obtained from the dihydrofurans of the formula I and, for example, beta-ionylideneethyltriphenylphosphonium bisulfate in a one-pot process. When less acidic triphenylphosphonium salts are used it may be necessary in some circumstances to follow the Wittig reaction by an acid treatment to cleave the dihydrofuran ring to the reaction product.

The invention therefore also relates to the use of the 2,5-bis(1,1-dialkoxy-2-propyl)-2,5-dihydrofurans of the formula I for preparing 2,7-dimethyl-2,4,6-octatrienedial and for preparing symmetric $C_{40}$-carotenoids of the formula IV

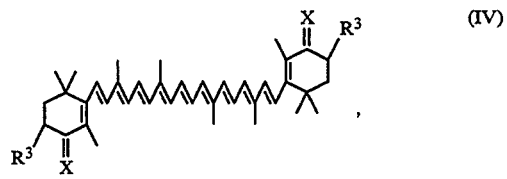

where $R^3$ is hydrogen or OH, and X is two hydrogens or one oxygen, and to a process for preparing $C_{40}$-carotenoids of the formula IV

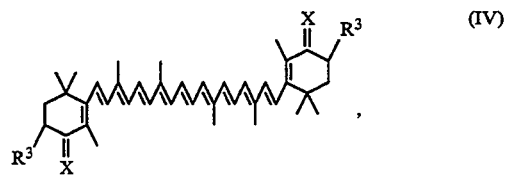

where $R^3$ is hydrogen or OH, and X is two hydrogens or one oxygen, which comprises initially adding a $C_{15}$-triphenylphosphonium salt of the formula V

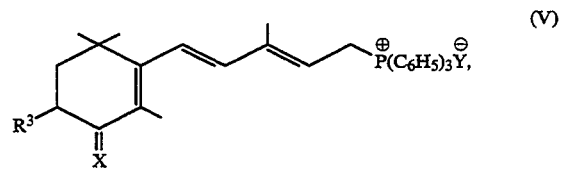

where $R^3$ and X have the abovementioned meanings, and Y is an anion, especially $HSO_4^\ominus$ or $Cl^\ominus$, to a 2,5-bis(1,1dialkoxy-2-propyl)-2,5-dihydrofuran of the formula I, and subjecting the dial which has been formed thereby from the bisacetal of the formula I by hydrolysis to a Wittig reaction with the carbenium ion formed from the triphenylphosphonium salt of the formula V by addition of a suitable strong base, and subsequently, where appropriate, treating with acid to cleave the dihydrofuran ring which may be still be present in the reaction product to give the required $C_{40}$-carotenoid.

EXAMPLE 1

0.5 g of $FeCl_3$ was introduced into 100 ml of ethyl acetate at $-10°$ C., and a mixture of 79 g (0.5 mol) of 2,5-diethoxy-2,5-dihydrofuran and 86 g (1 mol) of ethyl propenyl ether was added dropwise to this in such a way that the temperature remained at from $-8°$ to $-10°$ C. After the addition, 3 ml of triethanolamine were added to decompose the acid catalyst, the resulting precipitate was filtered off and the filtrate was distilled. 93 g of 2,5-bis(1,1-diethoxy-2-propyl)-2,5-dihydrofuran (mixture of isomers) were obtained with a boiling range from 120° to 180° C./1 mbar. This corresponds to a yield of 56% of theory.

EXAMPLE 2

32.5 g (0.25 mol) of 2,5-dimethoxy-2,5-dihydrofuran were added to a solution of 1 g of $ZnCl_2$ in 50 ml of ethyl acetate at 50° C. Then 43 g (0.5 mol) of ethyl propenyl ether were added dropwise at 50° C. The reaction mixture was stirred at 50° C. for 2 hours and then was found to contain 21.2% of 2,5-bis(1-methoxy-1-ethoxy-2-propyl)-2,5-dihydrofuran (random mixture). The amount of the reaction mixture was 126 g and thus the yield was 36% of theory.

EXAMPLE 3

32.5 g (0.25 mol) of 2,5-dimethoxy-2,5-dihydrofuran were added to a solution of 1 g of $SnCl_4$ and 0.4 g of benzonitrile in 25 ml of ethyl acetate at 10° C., and then 43 g (0.5 mol) of ethyl propenyl ether were added dropwise at from −8° to −10° C. over the course of 15 minutes (min). The reaction mixture was stirred at −10° C. for 20 minutes and then was found to contain 31% of 2,5-bis(1-methoxy-1-ethoxy-2-propyl)-2,5-dihydrofuran. The amount of the reaction mixture was 100 g and thus the yield was 42% of theory.

EXAMPLE 4

Synthesis of β-carotene 33 g (about 0.1 mol) of the 2,5-bis(1-methoxy-1-ethoxy-2-propyl)-2,5-dihydrofuran prepared as in Example 2 were added to a suspension, prepared in as EP 140, containing 0.2 mol of β-ionylideneethyltriphenylphosphonium bisulfate, and the resulting mixture was stirred at 80° C. for 6 hours (h). It was then cooled to room temperature (RT), and, at RT, 50 ml of a 25% strength aqueous solution of ammonia were added dropwise over the course of 30 min. After 2 h, 300 ml of heptane were added, the mixture was heated to 60° C. and then about 500 ml of 80% methanol were added to obtain a clear lower phase. This phase contained the salts and triphenylphosphine oxide and was separated off. The upper phase which contained the β-carotene in solution or suspension was washed three times with 400 ml of 80% methanol and subsequently distilled to remove sufficient heptane to produce a stirrable suspension of β-carotene in heptane. This suspension was refluxed for 24 h to isomerize the β-carotene to the all-trans form. The mixture was cooled to RT, diluted with heptane and filtered with suction. 19 g of crystalline β-carotene complying with the specification were obtained. The yield of all-trans-β-carotene was 35% based on the β-ionylideneethyltriphenylphosphonium salt. The mother liquor still contained 9 g of a cis/trans isomer mixture of β-carotene. Thus the overall yield was 52% of theory. The process has not yet been optimized.

We claim:

1. A process for preparing symmetric $C_{40}$-carotenoids of the formula IV

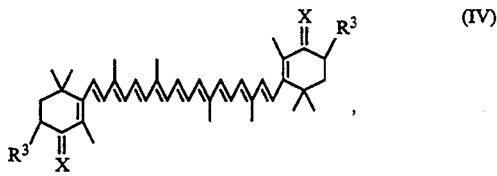

where $R^3$ is hydrogen or OH, and X is two hydrogens or one oxygen, which comprises adding a $C_{15}$-triphenylphosphonium salt of the formula V

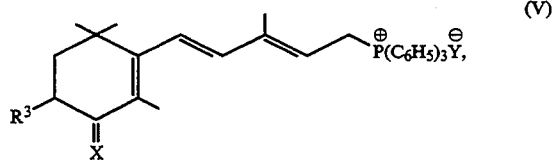

where $R^3$ is hydrogen or OH, X is two hydrogens or one oxygen, and Y is an anion, to a 2,5-bis(1,1-dialkoxy-2-propyl)-2,5-dihydrofuran of the formula I

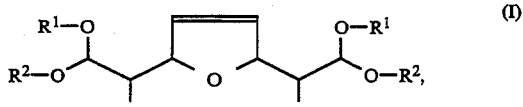

where $R^1$ and $R^2$ are identical or different and are alkyl of 1 to 4 carbons to form a reaction product containing a diacetal and a triphenylphosphonium salt; adding a strong base to the reaction product to convert the triphenylphosphonium salt to a carbenium ion; hydrolyzing the diacetal to a dialdehyde; subjecting the dialdehyde and the carbenium ion to a Wittig reaction to prepare a Wittig reaction product; and converting the Wittig reaction product to the $C_{40}$-carotenoid by acid treatment.

* * * * *